US012807635B2

(12) United States Patent
Zheng et al.

(10) Patent No.: US 12,807,635 B2
(45) Date of Patent: Nov. 24, 2026

(54) PURIFICATION METHOD FOR SUCRALOSE-6-ETHYL ESTER

(71) Applicant: ANHUI JINHE INDUSTRIAL CO., LTD., Chuzhou City (CN)

(72) Inventors: Xuelian Zheng, Chuzhou City (CN); Dong Wang, Chuzhou City (CN); Yongle Chen, Chuzhou City (CN)

(73) Assignee: ANHUI JINHE INDUSTRIAL CO., LTD., Chuzhou City (CN)

( * ) Notice: Subject to any disclaimer, the term of this patent is extended or adjusted under 35 U.S.C. 154(b) by 447 days.

(21) Appl. No.: 18/386,643

(22) Filed: Nov. 3, 2023

(65) Prior Publication Data

US 2024/0067671 A1 Feb. 29, 2024

Related U.S. Application Data

(63) Continuation of application No. PCT/CN2021/092168, filed on May 7, 2021.

(51) Int. Cl.
*C07H 1/06* (2006.01)
*C07H 3/04* (2006.01)

(52) U.S. Cl.
CPC ................. *C07H 1/06* (2013.01); *C07H 3/04* (2013.01)

(58) Field of Classification Search
None
See application file for complete search history.

(56) References Cited

FOREIGN PATENT DOCUMENTS

| | | | | | |
|---|---|---|---|---|---|
| CN | 109180748 | A | * | 1/2019 | ............... C07H 1/00 |
| CN | 109776627 | A | | 5/2019 | |
| CN | 112638924 | A | | 4/2021 | |
| WO | 2009137192 | A3 | | 2/2010 | |

* cited by examiner

*Primary Examiner* — Traviss C McIntosh, III
(74) *Attorney, Agent, or Firm* — IPro, PLLC

(57) ABSTRACT

Disclosed in the present disclosure is a purification method for sucralose-6-ethyl ester, and the method comprises: a secondary water boiling step: taking a sucralose-6-ethyl ester mother liquor, which has been subjected to boiling with water and a negative pressure treatment, adding a predetermined proportion of water to the sucralose-6-ethyl ester mother liquor, fully stirring and heating for boiling with water, and after stirring and boiling with water for a predetermined time, carrying out solid-liquid separation to obtain a secondary water-boiled mother liquor in which sucralose-6-ethyl ester is dissolved; a phase separating extraction step: leaving the secondary water-boiled mother liquor to stand for phase separation, taking the separated upper phase, extracting with an alkane extractant at a predetermined temperature, and removing residual white oil in the upper phase; a recrystallizing purification step: evaporating a lower-layer effluent obtained from extraction, so as to obtain a solid, and purifying the solid by means of recrystallization to obtain sucralose-6-ethyl ester; and a recycling step: separating the extracted upper-layer effluent, recovering the alkane extractant, and circulating the alkane extractant for use in the phase separation and extraction step. The method is simple, efficient and of low cost, and can effectively remove trace white oil and improve the purity of sucralose-6-ethyl ester.

10 Claims, 1 Drawing Sheet

PURIFICATION METHOD FOR SUCRALOSE-6-ETHYL ESTER

TECHNICAL FIELD

The present disclosure relates to the technical field of sugar production industry, and in particular relates to a method for purifying sucralose-6-ethyl ester.

BACKGROUND OF THE INVENTION

In the production process of sucralose, the solution of chlorination and neutralization obtained in the chlorination section contains impurities such as trichloroethane and dimethylformamide (DMF), which needs to be removed by retraction with white oil. White oil is a mixture of liquid hydrocarbons, mainly a mixture of saturated cycloalkanes and saturated chain alkanes, which is obtained by refining of petroleum or is obtained by normal pressure and reduced pressure fractionation, solvent extraction, dewaxing and hydrofining of crude oil, with relevant industrial standards such as "NB/SH/T 0006-2017 industrial mineral oil".

In the traditional process, the sucralose-6-ethyl ester product in the high-temperature chlorination section of sucralose needs to be boiled with water once after extraction with white oil, subjected to negative pressure to remove a small amount of trichloroethane residue, then repeatedly crystallized with ethyl acetate, and then dissolved, decolorized, deesterified, cooled to crystallize and centrifuged to obtain a refined sucralose-6-ethyl ester product, as described in Chinese patent CN109180748A. However, it is found in the production that after extraction with white oil, trace white oil will remain in the refined sucralose-6-ethyl ester product, which affects the quality of the subsequent sucralose product, and thus it is also necessary to repeatedly recrystallize the refined sucralose-6-ethyl ester product so as to just remove the trace white oil. Therefore, the amount of solvents used in the purification process of the sucralose-6-ethyl ester product is increased due to the trace white oil introduced by extraction in the chlorination section, which brings certain burden and influence on production and environment.

At present, the specialized method for removing white oil in the sucralose-6-ethyl ester product is rarely reported, and reports available about purifying sucralose-6-ethyl ester such as CN101328195 and CN101709069 usually use only solvents such as esters to purify sucralose-6-ethyl ester by crystallization, for example ethyl acetate and butyl acetate which are commonly used, failing to avoid the inclusion of white oil throughout in terms of effect.

SUMMARY OF THE INVENTION

Considering the problems of white oil residue in the sugar production process of sucralose in the prior art, the present application provides a method for purifying sucralose-6-ethyl ester, so as to overcome the above-mentioned problems.

In order to achieve the above purpose, the present application adopts the following technical solutions:

A method for purifying sucralose-6-ethyl ester, wherein white oil was used as an extractant in the chlorination section of the sucralose-6-ethyl ester preparing process, and the method comprises:

performing a secondary water boiling step: taking a sucralose-6-ethyl ester mother liquor obtained after water boiling and a negative pressure treatment, adding a predetermined proportion of water into the sucralose-6-ethyl ester mother liquor, fully stirring, heating for water boiling, and carrying out solid-liquid separation after stirring for a predetermined time to obtain a secondary water-boiled mother liquor with sucralose-6-ethyl ester dissolved in;

performing a phase separating extraction step: standing the secondary water-boiled mother liquor for phase separation, taking the upper phase after the phase separation, using an alkane extractant for extraction at a predetermined temperature, and removing the white oil residue of the upper phase;

performing a recrystallizing purification step: evaporating the lower-layer effluent obtained after the extraction to obtain a solid, and purifying the solid by recrystallization to obtain sucralose-6-ethyl ester;

and performing a recycling step: separating the upper-layer effluent obtained after the extraction, recovering the alkane extractant and circulating the alkane extractant to the phase separating extraction step for use.

Optionally, in the secondary water boiling step, the heating temperature is 40-90° C. the stirring rate is 200-400 r/min, and the stirring time is 0.5-2 h.

Optionally, in the secondary water boiling step, adding a predetermined proportion of water into the sucralose-6-ethyl ester mother liquor comprises:

adding the predetermined proportion of water gradually with stirring.

Optionally, in the secondary water boiling step, the water content is 30-90 wt % in the sucralose-6-ethyl ester mother liquor obtained after water boiling and the negative pressure treatment.

Optionally, in the secondary water boiling step, adding a predetermined proportion of water into the sucralose-6-ethyl ester mother liquor comprises:

adding water having a mass of 5-90% of the mass of the sucralose-6-ethyl ester mother liquor into the sucralose-6-ethyl ester mother liquor.

Optionally, in the phase separating extraction step, the alkane extractant used is one or more of cyclopentane, n-hexane, cyclohexane, isohexane, n-heptane, cycloheptane and isoheptane.

Optionally, in the phase separating extraction step, the feed volume ratio of the upper phase after the separation of the mother liquor to the alkane extractant is 1:0.2-1, and the extraction temperature is 20-40° C.

Optionally, in the recrystallizing purification step, purifying the solid by recrystallization to obtain sucralose-6-ethyl ester comprises:

recrystallizing the solid with ethyl acetate to obtain sucralose-6-ethyl ester.

Optionally, in the phase separating extraction step, taking the upper phase after the phase separation and using an alkane extractant for extraction at a predetermined temperature comprises: feeding the upper phase after the phase separation from the upper edge of the extraction tower, feeding the alkane extractant from the lower edge of the extraction tower, and carrying out the extraction in the extraction tower.

Optionally, the method further comprises:

recovering the solid substance obtained by the solid-liquid separation in the secondary water boiling step, and using it as a raw material again for the secondary water boiling with the sucralose-6-ethyl ester mother liquor.

In summary, the present application has the following beneficial effects:

According to the purification method of the present disclosure, in the purification process, the mother liquor of the chlorination section after being extracted with white oil is added with water for secondary water boiling and kept static for phase separation after the solid-liquid separation, the upper phase is extracted with alkane, such treatment can remove solid residues in the mother liquor, precipitate bottom tar and other impurities and meanwhile remove the trace white oil residue in the mother liquor, and finally a sucralose-6-ethyl ester crystal with higher purity is obtained through separation and recrystallization. The method is simple and efficient, the obtained sucralose-6-ethyl ester crystal is almost free of white oil residue, and the white oil removing process is only water boiling and extraction, not related to crystallization process, so that the crystallization frequency of the crystallization process in the later stage can be reduced, the usage of solvents is reduced, the quality of the final sucralose product is improved, and the method has high industrial application value.

Figure 1:
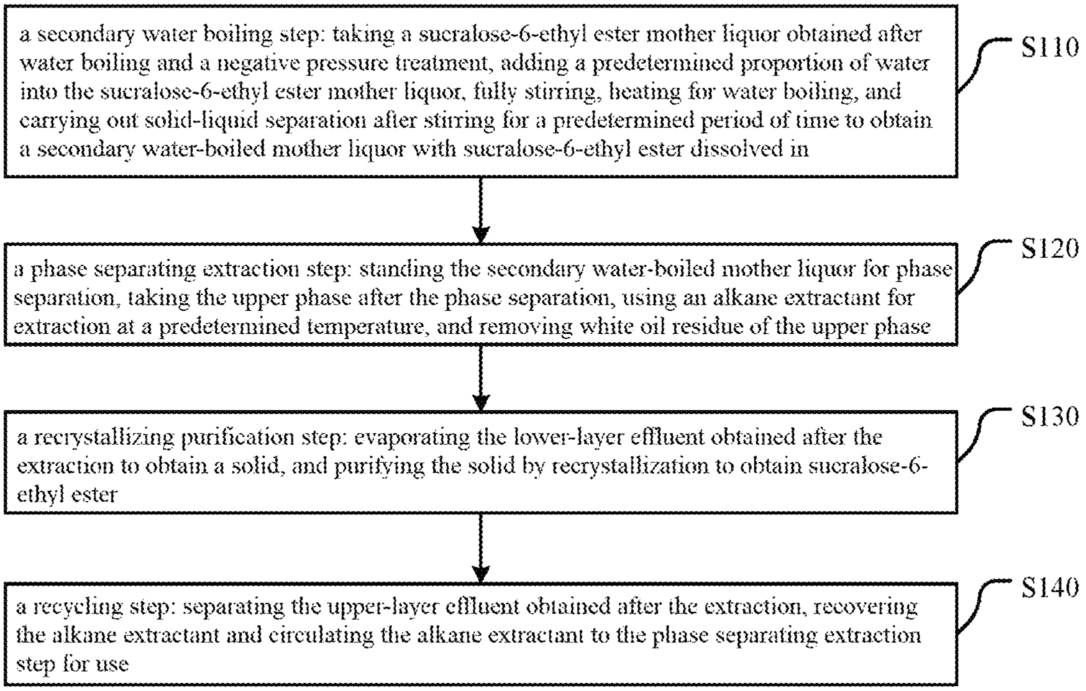
FIG. 1 is a flowchart of steps of a purification method for sucralose-6-ethyl ester according to an embodiment of the present disclosure.

In the drawings; E-1, a mixing kettle; H-1, a solid-liquid separator; E-2, a liquid-phase separator; E-3, an extraction tower; E-4, an evaporator; and E-5, a solvent recovering tower.

DETAILED DESCRIPTION OF THE EMBODIMENTS

In order to make the objectives, technical solutions and advantages of the present disclosure clearer, the embodiments of the present disclosure will be further described in detail below with the accompanying drawings.

In the traditional purification process of sucralose-6-ethyl ester, the final product is still mixed with trace white oil, which may be caused by the three aspects: 1, in the process of extracting trichloroethane and dimethylformamide with white oil, trichloroethane and DMF contained in the undissolved crude product of sucralose-6-ethyl ester carry trace white oil due to the encapsulation effect of the solid; 2, in the phase separating process, part of the white oil can be mixed in the sucralose-6-ethyl ester aqueous phase in the form of droplet due to equipment or operation problems; and 3, after early-stage treatment, a large amount of trichloroethane and DMF remain in the crude product of sucralose-6-ethyl ester, and a two-phase distribution is formed after white oil is dissolved. Therefore, in the traditional sugar production process, the method for refining the mother liquor after being extracted with white oil to prepare the sucralose-6-ethyl ester crystal cannot overcome the influence of the trace white oil, so that more recrystallization processes are needed, and the solvent cost and the environmental cost are relatively high.

Therefore, the present application provides a purification method for sucralose-6-ethyl ester. The technical concept of the present application is: in the purification process, the mother liquor of the chlorination section after being extracted with white oil was added with water for secondary water boiling, and kept standing for phase separation after solid-liquid separation, the upper phase was extracted with alkane, such treatment can remove solid residues in the mother liquor, separate bottom tar and other impurities out and meanwhile remove the trace white oil residue in the mother liquor, and finally a sucralose-6-ethyl ester crystal with higher purity is obtained through separation and recrystallization.

The purification method for sucralose-6-ethyl ester of the present application is simple and efficient, the sucralose-6-ethyl ester crystal obtained by crystallization is almost free of white oil residue, and the removing process of white oil is only water boiling and extraction, not related to crystallization process, so that the crystallization frequency of the crystallization process in the later stage can be reduced, the usage of the solvent is reduced, the quality of the final product of sucralose is improved, and the method has high industrial application value.

FIG. 1 shows an exemplary embodiment of a method for purifying sucralose-6-ethyl ester according to the present application, wherein white oil was used as an extractant in the chlorination section of the sucralose-6-ethyl ester preparation process, and the method comprises: A secondary water boiling step S110: taking a sucralose-6-ethyl ester mother liquor obtained after water boiling and a negative pressure treatment, adding a predetermined proportion of water into the sucralose-6-ethyl ester mother liquor, fully stirring, heating for water boiling, and carrying out solid-liquid separation after stirring for a predetermined time to obtain a secondary water-boiled mother liquor with sucralose-6-ethyl ester dissolved in. Thereinto, the sucralose-6-ethyl ester mother liquor obtained in the chlorination section is a solid-liquid mixture, in the present application the solubility of sucralose-6-ethyl ester in the mother liquor can be increased by adding water and heating, so as to solve the problem of low solubility of sucralose-6-ethyl ester in water at normal temperature, and meanwhile impurities such as tar can be better separated from the mother liquor by heating and boiling.

A phase separating extraction step S120: standing the secondary water-boiled mother liquor for phase separation, taking the upper phase after the phase separating, using an alkane extractant for extraction at a predetermined temperature, and removing the white oil residue of the upper phase, so as to overcome the influence of the trace white oil in the traditional process.

A recrystallizing purification step S130: evaporating the lower-layer effluent after being extracted to obtain a solid, wherein the solid is a crude product of sucralose-6-ethyl after removal of white oil impurities, and purifying the solid by recrystallization to obtain sucralose-6-ethyl ester.

A recycling step S140: separating the upper-layer effluent after being extracted, recovering the alkane extractant and circulating the alkane extractant to phase separating extraction step for use. Through the recycling step, the present application realizes the recycling of the extractant, and further reduces the production cost and the environmental cost.

In some embodiments of the present application, in the secondary water boiling step S110, the heating temperature for water boiling is 40-90° C., the stirring rate is 200-400 r/min, and the stirring time for water boiling is 0.5-2 h. Through secondary water boiling, the bottom tar and other impurities can be better precipitated, and layering separation and white oil extraction of the mother liquor in subsequent steps are facilitated.

In some embodiments of the present application, in the secondary water boiling step S110, adding a predetermined proportion of water into the sucralose-6-ethyl ester mother liquor comprises: adding the predetermined proportion of water gradually with stirring.

More preferably, in the secondary water boiling step S110, adding a predetermined proportion of water into the sucralose-6-ethyl ester mother liquor comprises: adding water having a mass of 5-90% of the mass of the sucralose-6-ethyl ester mother liquor into the sucralose-6-ethyl ester mother liquor.

By controlling the heating temperature, the water consumption and the stirring time for water boiling in the above embodiment, an effective pretreatment of the impurities in the sucralose-6-ethyl ester mother liquor can be realized, the precision of the phase separation of the sucralose-6-ethyl ester mother liquor and the extraction separation degree of white oil are improved, providing a basis for removing the trace white oil and preparing products with higher purity.

In some embodiments of the present application, in the secondary water boiling step S110, the water content is 30-90 wt % in the sucralose-6-ethyl ester mother liquor obtained after water boiling and the negative pressure treatment.

In one embodiment of the present application, in the phase separating extraction step S120, the alkane extractant used is one or more of cyclopentane, n-hexane, cyclohexane, isohexane, n-heptane, cycloheptane and isoheptane. Thereinto, alkanes such as cyclopentane, n-hexane, cyclohexane, isohexane, n-heptane, cycloheptane and isoheptane can fully extract the trace white oil in the upper phase after phase separation, and no newer impurities are introduced.

In some embodiments of the present application, in the phase separating extraction step S120, the feed volume ratio of the upper phase after the separation of the mother liquor to the alkane extractant is 1:0.2-1, and the extraction temperature is 20-40° C.

Specifically, in the phase separating extraction step S120, taking the upper phase after the phase separation and using an alkane extractant for extraction at a predetermined temperature comprises: feeding the upper phase after phase separation from the upper edge of the extraction tower, feeding the alkane extractant from the lower edge of the extraction tower, and carrying out the extraction in the extraction tower.

In some embodiments of the present application, in the recrystallizing purification step S130, purifying the solid by recrystallization to obtain sucralose-6-ethyl ester comprises: recrystallizing the solid with ethyl acetate to obtain sucralose-6-ethyl ester.

In some embodiments of the present application, the method further comprises: recovering the solid substance obtained by the solid-liquid separation in the secondary water boiling step S110, and using it as a raw material again for the secondary water boiling with the sucralose-6-ethyl ester mother liquor. Since the solid is mainly the undissolved sucralose-6-ethyl ester, by recovering the solid as a raw material after filtration, the yield of the final product can be increased.

Figure 2:
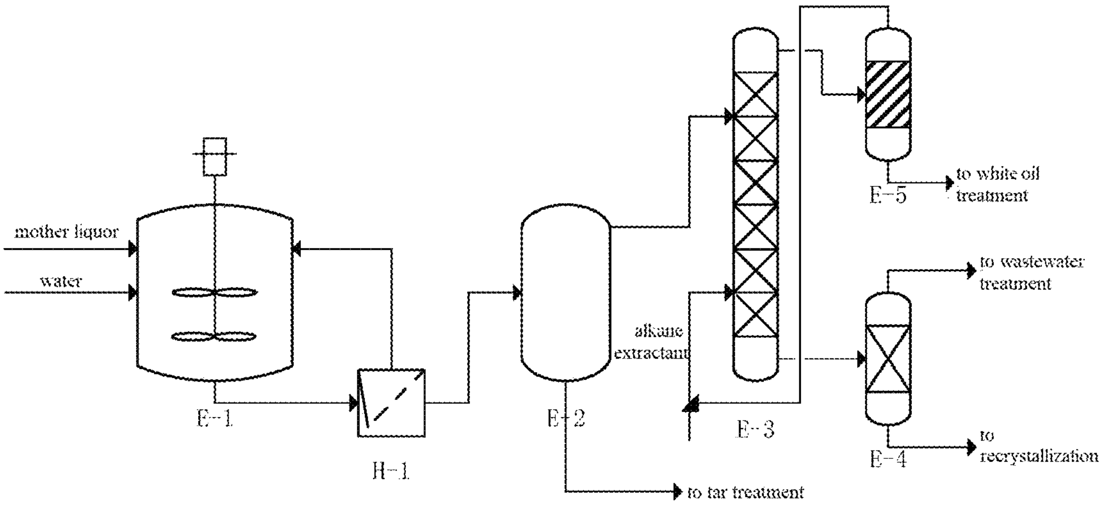
FIG. 2 is a process flow diagram of a purification method for sucralose-6-ethyl ester according to an embodiment of the present disclosure.

FIG. 2 is a process flow diagram of an exemplary embodiment of a purification method for sucralose-6-ethyl ester according to the present application. Thereinto, the solid-liquid separator H-1, the liquid-phase separator E-2, the evaporator E-4, the solvent recovering tower E-5 and so on are all conventional towers, and the operating parameters of the above-mentioned towers are not special for the present disclosure. With reference to FIG. 2, the process of the method embodiment of the present application is briefly described as follows:

Firstly, in a traditional sugar production process using white oil as an extractant in a chlorination section, a sucralose-6-ethyl ester mother liquor being boiled with water and subjected to negative pressure to remove trichloroethane is selected as a raw material, and it follows by (1) adding the mother liquor into the mixing kettle E-1, adding a small amount of water, fully stirring, and heating for water boiling; after stirring for a certain time, separating in the solid-liquid separator H-1, recovering the solid to the mixing kettle E-1, and standing the mother liquor in the liquid phase separator E-2;

(2) then removing the brown tar lower phase, and feeding the upper phase from the upper edge of the extraction tower E-3 after standing the mother liquor in the liquid-phase separator E-2 for layering; feeding the alkane extractant from the lower edge of the extraction tower, extracting at a certain temperature with a certain proportion of the two, taking an aqueous solution of sucralose-6-ethyl ester without white oil at the bottom of the extraction tower, and taking an alkane mixed solution (containing extracted white oil) at the top of the tower;

(3) feeding the extraction liquid taken at the bottom of the extraction tower into the evaporator E-4 for evaporation to obtain a solid, carrying out recrystallization section with ethyl acetate to obtain a refined sucralose-6-ethyl ester crystal, and carrying out wastewater treatment to the evaporated condensate water; and (4) feeding the alkane mixed solution taken at the top of the extraction tower into the solvent recovering tower E-5, recovering the alkane taken at the top of the solvent recovering tower to the extraction tower, and carrying out treatment to impurities such as white oil taken at the bottom of the tower.

By means of the purification method of the present application, the purity of sucralose-6-ethyl ester can be improved, thereby facilitating the next reaction and ensuring the quality of the final product sucralose; in addition, the purification method of the present application can effectively remove white oil and reduce the frequency of crystallization in the later stage, so as to reduce solvent consumption and reduce production cost; meanwhile, the method can also remove polymers and other impurities of the raw materials at the same time, thereby improving the product quality and recrystallization efficiency; and finally, by reducing the crystallization frequency and recovering the extractant, the producing of wastewater is reduced, and the environmental protection burden is effectively reduced.

Some embodiments applying the method of the present application are shown below.

Thereinto, sucralose-6-ethyl ester was obtained by esterification, chlorination and crystallization of sucrose in a sucralose production process, and the purity of the sucralose-6-ethyl ester was detected by a high performance liquid chromatograph (analysis and determination conditions of high performance liquid chromatography: Japan Shimadzu high performance liquid chromatograph, with RID-10A differential refraction detection, LC-10ADVP high pressure pump and CTO-10 ASVP incubator; chromatographic column: Agilent XDB C18 column (250 mm×4.6 mm, 5 μm); mobile phase: methanol-ultrapure water (4.5:5.5); column temperature: 45° C.; flow: 1.0 mL/min, wherein the quantity of methanol (chromatographically pure), ultrapure water and every standard substance was determined by external standard method). The purity of cyclopentane, n-hexane, cyclohexane, isohexane, n-heptane, cycloheptane, isoheptane and other raw materials used in every embodiment is greater than 99%, commercially available.

The white oil untreated group used as the comparison in every embodiment was a blank comparison group without carrying out the secondary water boiling and the subsequent phase separating extraction steps of the present disclosure, and the treatment process thereof was as follows: the sucralose-6-ethyl ester mother liquor being boiled with water only once and subjected to negative pressure to remove trichloroethane residue was only purified by recrystallizing purification with the same frequency as the corresponding embodiment, without carrying out the secondary water boiling and the subsequent phase separating extraction steps of the present disclosure.

Embodiment 1

It of a sucralose-6-ethyl ester mother liquor with a water content of 30% was added into the mixing kettle E-1, and heated for water boiling at 40° C., specifically, water of 90% of the mass of the mother liquor was added at a stirring rate of 300 r/min, and it was fully stirred. After stirring for 0.5 h, through separation in the solid-liquid separator H-1, the solid was recovered to the mixing kettle E-1, and the mother liquor was fed into the liquid phase separator E-2 to stand; the mother liquor was subjected to standing and was layered in the liquid-phase separator E-2, then the brown tar lower phase was removed, and the upper phase was fed from the upper edge of the extraction tower E-3; the cyclopentane extractant was fed from the lower edge of the extraction tower E-3, the ratio of the two was 1:0.5, the extraction was carried out at a temperature of 30° C., and a sucralose-6-ethyl ester aqueous solution without white oil was taken at the bottom of the tower and an alkane mixed solution was taken at the top of the tower after the extraction was completed; and the liquid taken at the bottom of the extraction tower was fed into the evaporator E-4 for evaporation, the obtained solid was cooled to be recrystallized with ethyl acetate twice, the obtained product was detected for the content of sucralose-6-ethyl ester, white oil and other components, the specific result was shown in Table 1.

TABLE 1

Comparison of the purity of sucralose-6-ethyl ester with white oil treated or untreated

| Item | Sucralose-6-ethyl ester/% | Water/% | Trichloroethane/% | White Oil/% | Others/% |
|---|---|---|---|---|---|
| White oil untreated | 89.11 | 4.32 | 3.32 | 0.013 | 3.237 |
| Embodiment 1 | 89.23 | 5.10 | 2.11 | 0.001 | 3.559 |

It can be seen from the above-mentioned data that the sucralose-6-ethyl ester prepared after treatment of Embodiment 1 applying the method of the present application, the white oil impurities thereof is significantly reduced, and it has overcome the influence of the trace white oil on the subsequent sugar production industry, without needs to use more solvents for multiple recrystallization, effectively reducing the usage of solvents and the frequency of crystallization, and reducing the production cost and the environmental cost.

Embodiment 2

2 t of a sucralose-6-ethyl ester mother liquor with a water content of 40% was added to the mixing kettle E-1, and heated for water boiling at 90° C., water of 80% of the mass of the mother liquor was added at a stirring rate of 400 r/min, and it was fully stirred. After stirring for 0.5 h, through separation in the solid-liquid separator H-1, the solid was recovered to the mixing kettle E-1, and the mother liquor was fed into the liquid phase separator E-2 to stand; the mother liquor was subjected to standing and layered in the liquid phase separator E-2, then the brown tar lower phase was removed, and the upper phase was fed from the upper edge of the extraction tower E-3; the cyclohexane extractant was fed from the lower edge of the extraction tower, the ratio of the two was 1:0.6, the extraction was carried out at the temperature of 25° C., and a sucralose-6-ethyl ester aqueous solution without white oil was taken at the bottom of the tower and an alkane mixed solution was taken from the top of the tower after the extraction was completed; and the liquid taken at the bottom of the extraction tower was fed into the evaporator E-4 for evaporation, the obtained solid was cooled to be recrystallized with ethyl acetate twice, the obtained product was detected for the content of sucralose-6-ethyl ester, white oil and other components, and the specific result was shown in Table 2.

TABLE 2

Comparison of the purity of sucralose-6-ethyl ester with white oil treated or untreated

| Item | Sucralose-6-ethyl ester/% | Water/% | Trichloroethane/% | White Oil/% | Others/% |
|---|---|---|---|---|---|
| white oil untreated | 86.47 | 5.08 | 3.97 | 0.021 | 4.459 |
| Embodiment 1 | 87.23 | 5.75 | 3.23 | 0.002 | 3.788 |

Embodiment 3

3t of a sucralose-6-ethyl ester mother liquor with a water content of 50% was added to the mixing kettle E-1, and heated for water boiling at 55° C., water of 65% of the mass of mother liquor was added at a stirring rate of 250 r/min, and it was fully stirred. After stirring for 1.5 h, through separation in the solid-liquid separator H-1, the solid was recovered to the mixing kettle E-1, and the mother liquor was fed into the liquid phase separator E-2 to stand; the mother liquor was subjected to standing and was layered in the liquid phase separator E-2, then the brown tar lower phase was removed, and the upper phase was fed from the upper edge of the extraction tower E-3; the isoheptane extractant was fed from the lower edge of the extraction tower, the ratio of the two was 1:0.8, the extraction was carried out at a temperature of 40° C., and a sucralose-6-ethyl ester aqueous solution without white oil was taken at the bottom of the tower and an alkane mixed solution was taken at the top of the tower after the extraction was completed; and the liquid taken at the bottom of the extraction tower was fed into an evaporator E-4 for evaporation, the obtained solid was cooled to be recrystallizated with ethyl acetate twice, the obtained product was detected for the content of sucralose-6-ethyl ester, white oil and other components, the specific result was shown in Table 3.

TABLE 3

| Comparison of the purity of sucralose-6-ethyl ester with white oil treated or untreated | | | | | |
|---|---|---|---|---|---|
| Item | Sucralose-6-ethyl ester/% | Water/% | Trichloroethane/% | White Oil/% | Others/% |
| White oil untreated | 88.89 | 4.99 | 4.21 | 0.028 | 1.882 |
| Embodiment 1 | 90.45 | 5.16 | 3.57 | 0.001 | 0.819 |

Embodiment 4

4t of a sucralose-6-ethyl ester mother liquor with a water content of 60% was added to the mixing kettle E-1, and heated for water boiling at 70° C., water of 45% of the mass of the mother liquor was added at a stirring rate of 200 r/min, and it was fully stirred. After stirring for 2 h, through separation in the solid-liquid separator H-1, the solid was recovered to the mixing kettle E-1, and the mother liquor was fed into the liquid phase separator E-2 to stand; the mother liquor was subjected to standing and was layered in the liquid phase separator E-2, then the brown tar lower phase was removed, and the upper phase was fed from the upper edge of the extraction tower E-3; the isohexane extractant was fed from the lower edge of the extraction tower, the ratio of the two was 1:1, the extraction was carried out at the temperature of 35° C., and a sucralose-6-ethyl ester aqueous solution without white oil was taken at the bottom of the tower and an alkane mixed solution was taken at top of the tower after the extraction was completed; and the liquid taken at the bottom of the extraction tower was fed into the evaporator E-4 for evaporation, the obtained solid was cooled to be recrystallized with ethyl acetate twice, the obtained product was detected for the content of sucralose-6-ethyl ester, white oil and other components, and the specific result was shown in Table 4.

TABLE 4

| Comparison of the purity of sucralose-6-ethyl ester with white oil treated or untreated | | | | | |
|---|---|---|---|---|---|
| Item | Sucralose-6-ethyl ester/% | Water/% | Trichloroethane/% | White Oil/% | Others/% |
| White oil untreated | 88.65 | 5.87 | 4.16 | 0.034 | 1.286 |
| Embodiment 1 | 90.38 | 6.00 | 3.01 | 0.002 | 0.608 |

Embodiment 5

1.5t of a sucralose-6-ethyl ester mother liquor with a water content of 70% was added to the mixing kettle E-1, and heated for water boiling at 85° C., water of 25% of the mass of the mother liquor was added at a stirring rate of 350 r/min, and it was fully stirred. After stirring for 0.5 h, through separation by the solid-liquid separator H-1, the solid was recovered to the mixing kettle E-1, and the mother liquor was fed into the liquid phase separator E-2 to stand; the mother liquor was subjected to standing and was layered in the liquid phase separator E-2, then the brown tar lower phase was removed, and the upper phase was fed from the upper edge of the extraction tower E-3; the n-hexane extractant was fed from the lower edge of the extraction tower, the ratio of the two was 1:0.2, the extraction was carried out at a temperature of 20° C., and a sucralose-6-ethyl ester aqueous solution without white oil was taken at the bottom of the tower and an alkane mixed solution was taken at the top of the tower after the extraction was completed; the liquid taken at the bottom of the tower was fed into the evaporator E-4 for evaporation, the obtained solid was cooled to be recrystallized with ethyl acetate twice, the obtained product was detected for the content of sucralose-6-ethyl ester, white oil and other components, and the specific result was shown in Table 5.

TABLE 5

| Comparison of the purity of sucralose-6-ethyl ester with white oil treated or untreated | | | | | |
|---|---|---|---|---|---|
| Item | Sucralose-6-ethyl ester/% | Water/% | Trichloroethane/% | White Oil/% | Others/% |
| White oil untreated | 89.74 | 3.98 | 4.55 | 0.015 | 1.715 |
| Embodiment 1 | 92.03 | 5.02 | 2.09 | 0.001 | 0.859 |

Embodiment 6

4.5 t of a sucralose-6-ethyl ester mother liquor with a water content of 80% was added to the mixing kettle E-1, and heated for water boiling at 75° C., water of 10% of the mass of the mother liquor was added at a stirring rate of 300 r/min, and it was fully stirred. After stirring for 2 h, through separation in the solid-liquid separator H-1, the solid was recovered to the mixing kettle E-1, and the mother liquor was fed into the liquid phase separator E-2 to stand; the mother liquor was subjected to standing and was layered in the liquid phase separator E-2, then the brown tar lower phase was removed, and the upper phase was fed from the upper edge of the extraction tower E-3; the n-heptane extractant was fed from the lower edge of the extraction tower, the ratio of the two was 1:0.3, the extracting was carried out at a temperature of 20° C., and a sucralose-6-ethyl ester aqueous solution without white oil was taken at the bottom of the tower and an alkane mixed solution was taken at the top of the tower after the extraction was completed; and the liquid taken at the bottom of the extraction tower was fed into the evaporator E-4 for evaporation, the obtained solid was cooled to be recrystallized with ethyl acetate twice, the obtained product was detected for the content of sucralose-6-ethyl ester, white oil and other components, the specific result was shown in Table 6.

TABLE 6

Comparison of the purity of sucralose-6-ethyl ester with white oil treated or untreated

| Item | sucralose-6-ethyl ester/% | Water/% | Trichloroethane/% | White Oil/% | Others/% |
|---|---|---|---|---|---|
| white oil untreated | 89.33 | 3.99 | 5.43 | 0.017 | 1.233 |
| Example 1 | 91.11 | 6.29 | 2.11 | 0.001 | 0.489 |

Embodiment 7

2.5 t of a sucralose-6-ethyl ester mother liquor with a water content of 90% was added to the mixing kettle E-1, and heated for water boiling at 60° C., water of 5% of the mass of the mother liquor was added at a stirring rate of 400 r/min, and it was fully stirred. After stirring for 1 h, through separation in the solid-liquid separator H-1, the solid was recovered to the mixing kettle E-1, and the mother liquor was fed into the liquid phase separator E-2 to stand; the mother liquor was subjected to standing and was layered in the liquid phase separator E-2, then the brown tar lower phase was removed, and the upper phase was fed from the upper edge of the extraction tower E-3; the cyclopentane extractant was fed from the lower edge of the extraction tower, the ratio of the two was 1:0.2, the extraction was carried out at 25° C., and a sucralose-6-ethyl ester aqueous solution without white oil was taken at the bottom of the tower and an alkane mixed solution was taken at the top of the tower after the extraction was completed; and the liquid taken at the bottom of the extraction tower was fed into an evaporator E-4 for evaporation, the obtained solid was cooled to be recrystallized with ethyl acetate twice, the obtained product was detected for the content of sucralose-6-ethyl ester, white oil and other components, and the specific result was shown in Table 7.

TABLE 7

Comparison of the purity of sucralose-6-ethyl ester with white oil treated or untreated

| Item | sucralose-6-ethyl ester/% | Water/% | Trichloroethane/% | White Oil/% | Others/% |
|---|---|---|---|---|---|
| White oil untreated | 87.37 | 6.70 | 2.12 | 0.009 | 3.801 |
| Embodiment 1 | 88.80 | 7.22 | 1.93 | 0.001 | 2.049 |

Embodiment 8

3.5 t of a sucralose-6-ethyl ester mother liquor with a water content of 55% was added to a mixing kettle E-1, and heated for water boiling at 80° C., water of 25% of the mass of the mother liquor was added at a stirring rate of 200 r/min, and it was fully stirred. After stirring for 1.5 h, through separation in the solid-liquid separator H-1, the solid was recovered to the mixing kettle E-1, and the mother liquor was fed into the liquid phase separator E-2 to stand; the mother liquor was subjected to standing and was layered in the liquid phase separator E-2, then the brown tar lower phase was removed, and the upper phase was fed from the upper edge of the extraction tower E-3; the cycloheptane extractant was fed from the lower edge of the extraction tower, the ratio of the two was 1:1, the extraction was carried out at the temperature of 25° C., and a sucralose-6-ethyl ester aqueous solution without white oil was taken at bottom of the tower and an alkane mixed solution was taken at the top of the tower after the extraction was completed; and the liquid taken at the bottom of the extraction tower was fed into the evaporator E-4 for evaporation, the obtained solid was cooled to be recrystallized with ethyl acetate twice, the obtained product was detected for the content of sucralose-6-ethyl ester, white oil and other components, and the specific result was shown in Table 8.

TABLE 8

Comparison of the purity of sucralose-6-ethyl ester with white oil treated or untreated

| Item | Sucralose-6-ethyl ester/% | Water/% | Trichloroethane/% | White Oil/% | Others/% |
|---|---|---|---|---|---|
| White oil untreated | 85.21 | 7.16 | 2.37 | 0.032 | 5.228 |
| Embodiment 1 | 87.39 | 7.87 | 1.93 | 0.002 | 2.808 |

As can be seen from the above embodiments, the method of the present application can significantly remove the white oil in the sucralose-6-ethyl ester product, and effectively improve the purity of the sucralose-6-ethyl ester, thereby overcoming the influence of the white oil residue on the sugar production process of sucralose, and improving the quality of the final sucralose product. And the method is simple and efficient, it can be realized without changing the original processes and equipments on a large scale, production cost and environment cost are low, and it can also control the complexity of the subsequent crystallization process.

The above is merely specific embodiments of the present disclosure, and under the above teachings of the present disclosure, a person skilled in the art may perform other improvements or modifications on the basis of the above embodiments. It should be understood by those skilled in the art that the above-mentioned specific description is merely a better explanation of the purpose of the present disclosure, and the scope of protection of the present disclosure shall be subject to the scope of protection of the claims.

What is claimed is:

1. A purification method for sucralose-6-ethyl ester, wherein white oil was used as an extractant in the chlorination section of the sucralose-6-ethyl ester preparation process, wherein the method comprises:

performing a secondary water boiling step: taking a sucralose-6-ethyl ester mother liquor obtained after water boiling and a negative pressure treatment, adding a predetermined proportion of water into the sucralose-6-ethyl ester mother liquor, fully stirring, heating for water boiling, and after stirring and boiling for a predetermined time, carrying out solid-liquid separation to obtain a secondary water-boiled mother liquor with sucralose-6-ethyl ester dissolved in;

performing a phase separating extraction step: standing the secondary water boiled mother liquor for phase separation, taking the upper phase after the phase separation, extracting with an alkane extractant at a predetermined temperature, and removing white oil residue in the upper phase;

performing a recrystallizing purification step: evaporating the lower-layer effluent obtained after the extraction to obtain a solid, and purifying the solid by recrystallization to obtain sucralose-6-ethyl ester;

and performing a recycling step: separating the upper-layer effluent obtained after the extraction, recovering the alkane extractant and circulating it to the phase separating extraction step for use.

2. The purification method according to claim 1, wherein in the secondary water boiling step, the heating temperature is 40-90° C., the stirring rate is 200-400 r/min, and the stirring time for water boiling is 0.5-2 h.

3. The purification method according to claim 1, wherein in the secondary water boiling step, adding a predetermined proportion of water into the sucralose-6-ethyl ester mother liquor comprises: adding the predetermined proportion of water gradually with stirring.

4. The purification method according to claim 1, wherein in the secondary water boiling step, the water content is 30-90 wt % in the sucralose-6-ethyl ester mother liquor obtained after water boiled and a negative pressure treatment.

5. The purification method according to claim 1, wherein in the secondary water boiling step, adding a predetermined proportion of water into the sucralose-6-ethyl ester mother liquor comprises: adding water having a mass of 5-90% of the mass of the sucralose-6-ethyl ester mother liquor into the sucralose-6-ethyl ester mother liquor.

6. The purification method according to claim 1, wherein in the phase separating extraction step, the alkane extractant used is one or more of cyclopentane, n-hexane, cyclohexane, isohexane, n-heptane, cycloheptane and isoheptane.

7. The purification method according to claim 1, wherein in the phase separation extraction step, the feed volume ratio of the upper phase obtained after the separation of the mother liquor to the alkane extractant is 1:0.2-1, and the extraction temperature is 20-40° C.

8. The purification method according to claim 1, wherein in the recrystallizing purification step, purifying the solid by recrystallization to obtain sucralose-6-ethyl ester comprises: recrystallizing the solid with ethyl acetate to obtain sucralose-6-ethyl ester.

9. The purification method according to claim 1, wherein in the phase separating extraction step, taking the upper phase after the phase separation and extracting with an alkane extractant at a predetermined temperature comprises: feeding the upper phase obtained after the phase separation from the upper edge of the extraction tower, feeding the alkane extractant from the lower edge of the extraction tower, and carrying out the extraction in the extraction tower.

10. The purification method according to claim 1, wherein the method further comprises: recovering the solid substance obtained by the solid-liquid separation in the secondary water boiling step, and using it as a raw material again for the secondary water boiling with the sucralose-6-ethyl ester mother liquor.

* * * * *